United States Patent [19]

Wieder

[11] 4,341,957
[45] Jul. 27, 1982

[54] FLUORESCENT ANTIBODY COMPOSITION FOR IMMUNOFLUOROMETRIC ASSAY

[75] Inventor: Irwin Wieder, Los Altos, Calif.

[73] Assignee: Analytical Radiation Corporation, Los Altos, Calif.

[21] Appl. No.: 635,411

[22] Filed: Nov. 26, 1975

[51] Int. Cl.³ .................. G01N 21/64; G09K 3/00
[52] U.S. Cl. .................. 250/461.2; 250/302; 250/365
[58] Field of Search .......... 250/461, 365, 302, 461 B; 424/2, 12

[56] References Cited

U.S. PATENT DOCUMENTS

| | | | |
|---|---|---|---|
| Re. 25,320 | 1/1963 | Lewis et al. | 250/365 |
| 3,449,571 | 6/1969 | Hoerman et al. | 250/365 |
| 3,473,027 | 10/1969 | Freeman et al. | 250/365 |
| 3,484,380 | 12/1969 | Kleinerman | 250/461 |
| 3,539,941 | 11/1970 | Halverson | 250/461 |
| 3,666,421 | 5/1972 | Price | 424/12 |
| 3,789,116 | 1/1974 | Kay | 424/7 |
| 3,826,619 | 7/1974 | Bratu | 250/302 |
| 3,853,987 | 12/1974 | Dreyer | 424/12 |
| 3,882,224 | 5/1975 | Forgione | 424/8 |
| 3,886,363 | 5/1975 | Ohnishi | 250/364 |
| 3,918,812 | 11/1975 | Holm | 250/365 |
| 3,992,631 | 11/1976 | Harte | 250/302 |
| 4,006,360 | 2/1977 | Mueller | 250/461 |
| 4,058,732 | 11/1977 | Wieder | 250/461 B |

OTHER PUBLICATIONS

"Gated Nanosecond . . . " by Brown et al., Analytical Chemistry vol. 46 No. 12 Oct. 1974 pp. 1690–1695.
Filipescu et al. (Filipescu), J. Phys. Chem. 68, 3324–3346 (1964).

*Primary Examiner*—Harold A. Dixon
*Attorney, Agent, or Firm*—William H. Benz; Thomas Schneck, Jr.

[57] ABSTRACT

A new family of fluorescent antibodies (FAB) and a method for their synthesis is disclosed for use in an apparatus and method wherein the effects of background fluorescence are virtually eliminated from fluorescence measurements. The novel fluorescent antibodies consist of antibodies conjugated with rare-earth chelates which have unique fluorescent properties. These fluorescent antibodies are useful because when excited with short pulses of light, they exhibit fluorescent decay times which are much longer than typical background fluorescence at room temperature and with a spectral width far narrower than typical background fluorescence.

22 Claims, 4 Drawing Figures

TYPICAL EXCITATION PULSE WITH DURATION OF 3 NANOSECONDS.

TYPICAL BACKGROUND FLUORESCENCE DECAY WITH LIFETIME OF 10 NANOSECONDS.

TIME (NANOSECONDS)

TYPICAL RARE EARTH FLUORESCENCE DECAY WITH LIFETIME OF 100 MICROSECONDS.

TIME (MICROSECONDS)

FLUORESCENT ANTIBODY COMPOSITION FOR IMMUNOFLUOROMETRIC ASSAY

BACKGROUND OF THE INVENTION a. Field of the Invention.

The invention relates to the field of the fluorescent detection of small quantities of molecules in the presence of background or competing fluorescence. In particular, the invention relates to a new fluorescent antibody, and a method which utilizes the unique fluorescent properties of the new fluorescent antibody to minimize the effect of background fluorescence thereby greatly increasing the effective sensitivity of fluorescent detection methods.

b. Prior Art.

The fluorescent antibody (FAB) technique was originated by Coons and co-workers in 1941. The original concept was to couple a dye to an antibody which could then bind to an antigen. In its initial forms it was primarily used to visualize or trace the distribution of certain antigens in tissues or on cells. The use of a fluorescent dye, in contrast with ordinary non-fluorescing dyes which had been previously used as markers, resulted in a thousand fold increase in sensitivity.

In the years that followed, the techniques of conjugating fluorescent dyes were improved and more stable dyes were synthesized. In 1950 and 1951 Coons and co-workers developed improved methods for synthesizing fluorescein isocyanate and conjugating it with antibodies. This, coupled with the development of readily available fluorescent microscopes, placed the FAB methodology on firm footing and paved the way for its extended use in medicine.

In the late 1950's three other important stable fluorescent dyes were developed, Rhodamine B200, 1-dimethylaminonaphthalene 5-sulfonyl chloride (DANS), and fluorescein isothiocyanate (FITC). To this date, however, the most commonly used dye in FAB work is FITC.

Until quite recently the FAB technique has been used primarily as a tracer, for visualization of the location of antigens on a sample using a fluorescent microscope. These uses were not quantitative; the fluorescence of the FAB was used only to indicate the presence or absence of a particular antigen or its distribution on tissue or a cell.

Presently, a considerable amount of effort is being expended to develop immunological methods which would enable the quantitative measurement of specific antigens in the blood or other body fluids. These antigens may be naturally occurring substances such as cancer antigens, renin, or thyroxine or administered drugs such as digoxin, or methotrexate.

One immunological test which has been successfully applied to assays requiring high sensitivity is radioimmunoassay (RIA). In RIA, antigen of the type to be assayed is labeled radioactively, allowed to compete for available antibodies with antigen to be assayed and after suitable procedures, radioactivity is measured and the amount of antigen present deduced. Though RIA is sufficiently sensitive for most subtle assays, it suffers from disadvantages because of the radioactive label. These disadvantages include extra care in handling radioactive material, the problem of disposal of radioactive wastes and the finite shelf life of radioactive antigens, typically 60 days.

The possibility of utilizing FAB instead of radioactively labeled antigens in immunoassay has been considered by workers in the field because of the extreme sensitivity of the fluorescence method, especially using laser excitation. However, the presence of background fluorescence of sample holders, reagents, administered drugs and organic material in the blood serum or urine has interfered with the attainment of the high sensitivity needed for immunofluorometric assay.

One method that has been suggested to increase sensitivity in immunofluorometric analysis is "mechanical amplification". This method utilizes microscopic balls labeled with fluorescent dyes and antibodies and is described in U.S. Pat. No. 3,853,987 issued to Dryer. The Dryer method attempts to increase the signal from the antigen-antibody complex.

In 1975, Wieder filed a co-pending patent application, Ser. No. 591,305, filed June 30, 1975 now U.S. Pat. No. 4,058,732, issued Nov. 15, 1977, in which he disclosed a method for improved fluorescent spectroscopy wherein target molecules whose presence is to be measured are combined with fluorescent molecules having a relatively long fluorescent decay lifetime. These tagged target molecules are excited with a pulse of ultraviolet or visible radiation and a detection system is gated on only after background fluorescence has substantially decayed, but while the fluorescent tag attached to the target molecules is still actively decaying. The amount of fluorescence tag emission which is measured is indicative of the target molecule content of the sample.

In that patent application, an apparatus for improved fluorescent spectrofluorometry was also disclosed which includes a pulsed excitation source and a gating means connected to a detection system for gating the detection system on after tagged target molecules have been excited and competing background fluorescence has substantially decayed. In an article in Analytical Chemistry 46, 1960 (1974) R. E. Brown et al. have disclosed a gated spectrofluorometric apparatus.

In Wieder's application two examples of a tagging agent were disclosed. One example was the class of rare-earth organo complexes, i.e. rare-earth chelates, which are non-specific target tags and have fluorescent lifetimes of 100 to 800 microseconds. The other example, was a FAB which consists of a target specific antibody conjugated with pyrenebutyrate. However, even though this FAB has a fluorescent lifetime of about 200 nanoseconds which is longer than expected background fluorescence, it limits the delay time before the detection apparatus is turned on, thus limiting the extent to which background fluorescence has decayed before the measurement begins.

An object of the invention is to devise a new FAB family with a longer decay lifetime than any prior FAB for use in an immunofluorometric assay and other applications.

SUMMARY OF THE INVENTION

The above object is met with a new FAB family which consists of antibodies conjugated with rare-earth chelates. The selected antibody is one specific to a target antigen to be measured, and the rare-earth chelate selected is one having narrow spectral, long-lived fluorescence at room temperature upon suitable excitation.

The FAB can be used in the fluorescent detection of a target substance in the presence of background fluorescence. The method includes a step of tagging target substances with the FAB which has a long fluorescent decay time compared with the decay time of ambient substances, and a second step of separating excess FAB from the target substance.

In a third step, the tagged substances are excited with pulses of radiation having the appropriate spectral distribution, i.e. within the excitation spectrum of the tagged substance, each pulse having a pulse duration or cutoff duration which is short compared with the relatively long fluorescent decay time of the fluorescent antibody. Then a fluorescence detection system is gated on only after the fluorescence of ambient subtances, which cause the deleterious competing fluorescence, has substantially decayed.

Figure 1:
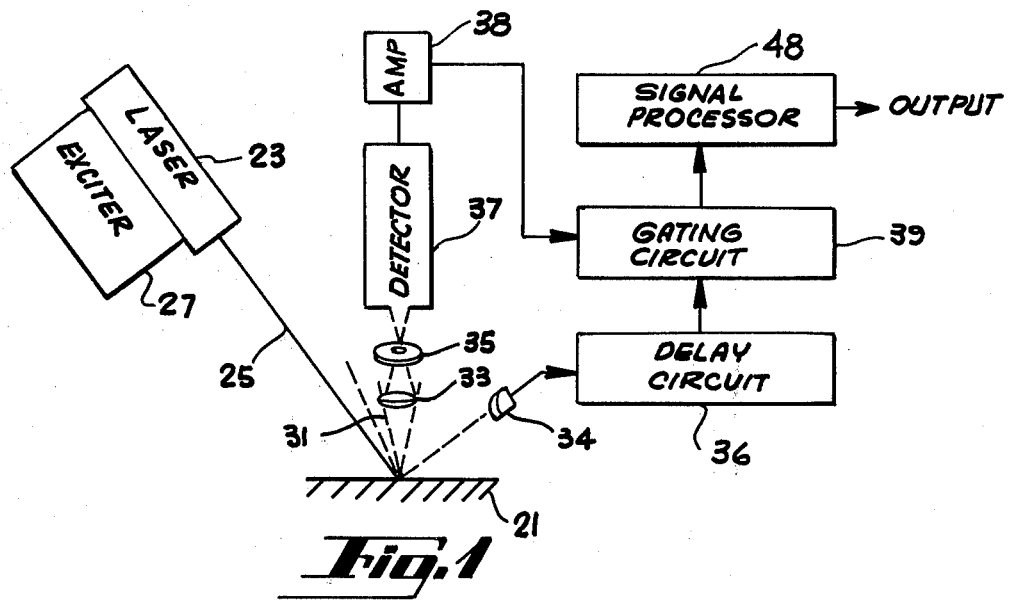
FIG. 1 is a plan view of the apparatus in which the composition of the present invention may be used.

DESCRIPTION OF THE PREFERRED EMBODIMENT a. The Fluorescent Antibody. The new FAB family of the present invention is characterized by long lived, narrow spectral fluorescence. The new FABs consist of fluorescent antibodies conjugated with rare-earth chelates.

The procedures selected for the attachment of rare-earth chelates to antibodies satisfy several criteria. A chelating ligand, a chemical group which coordinates (binds) rare-earth ions should conjugate readily with antibody under mild conditions to give a covalently bound, irreversible adduct. The coupling procedure and presence of a label on the antibody should not reduce antibody specificity and reactivity to any significant degree. The rare-earth chelate selected for its fluorescent properties should be the type which exhibits good quantum efficiency at room temperature and sharp spectral, long lived fluorescence characteristics of the rare-earth ion.

For most chelating ligands this restricts the choice of rare-earth to europium +3, hereafter referred to as Eu(III), and terbium +3, hereafter referred to as Tb(III), since these rare-earth ions show favorable positions of their low lying excited states relative to the lowest triplet state of the donor chelating ligand molecules. This enhances the mechanism by which these rare-earth ions fluoresce, namely, the absorption of ultraviolet energy in the ligand singlet system, transfer of the energy to the ligand triplet system and subsequent transfer of energy to the rare-earth ion states. This process is discussed more fully by R. F. Whan and G. A. Crosby, J. Molec. Spect. 8, 315–327, (1962), incorporated by reference herein.

Eu(III) and Tb(III) chelates have exhibited the most intense fluorescence at room temperature in both solid state and in solution when combined with a variety of ligands. These various ligands which can be used are discussed more fully for example by S. I. Weissman, J. Chem. Phys., 10, 214–217 (1942); by R. A. Gudmundsen et al., J. Chem. Phys., 39, 272 (1963); and by M. L. Bhaumik and C. L. Telk, J. Opt. Soc. Amer., 54, 1211, (1964) and are incorporated by reference herein.

Exemplary rare-earth chelates suitable for attaching to antibodies for immunoassay purposes are Eu(III)tris(hexafluoroacetylacetonate), Eu(III)tris- or tetrakis(thenoyltrifluoroacetonate), Eu(III)tris- or tetrakis (benzoyltrifluoroacetonate), and Tb(III)tris(acetylacetonate).

As a first example, Eu(III)tris(thenoyltrifluoroacetonate) is selected as a fluorescent chelate which is to be attached to an antibody or other protein.

The first step is the synthesis of a modified thenoyltrifluoroacetonate ligand, denoted 1 below, which has an aminomethyl group on the 5 position of the thiophene ring.

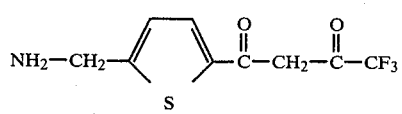

Compound 1 can be synthesized by established procedures for the synthesis of β diketones. The first step in the procedure is the reductive synthesis of 2-acetyl-5-(aminomethyl) thiophene, compound 5 below, from the blocked 5-cyano-2-acetyl thiophene, compound 4 below.

Starting with the readily available compound, denoted 2, 5-iodo-2-acetylthiophene

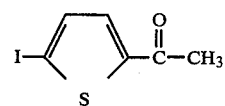

and using a procedure described by S. Nishimura and E. Imoto, Nippon Kagaku Zasshi 82, 1411 (1961), incorporated by reference herein, one generates 5-cyano-2-acetylthiophene denoted 3 below,

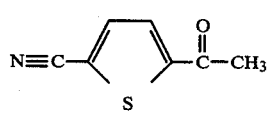

The "blocked" form is then generated according to standard methods. See for example W. S. Johnson et al., J. Amer. Chem. Soc. 78, 6300, (1956), incorporated by reference herein. This results in a compound, denoted 4 below,

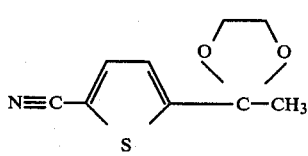

Compound 4 is then reduced with available methods such as the one described by R. F. Nystrom and W. G. Brown, J. Amer. Chem. Soc. 70, 3738 (1948), incorporated by reference herein, and then "deblocked" (see for example W. S. Johnson et al. above) to give 2-acetyl-5-(aminomethyl)thiophene, 5,:

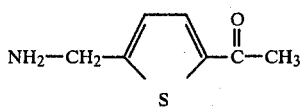

Then using standard Claisen condensation techniques, such as described by J. C. Reid and M. Calvin, J. Amer. Chem. Soc. 72, 2948 (1950), incorporated by reference herein, the chelating ligand 1 is synthesized, abbreviated hereafter as TTFA-NH$_2$.

The Eu(III) complex containing the anion of one functionalized ligand, TTFA-NH$_2$, and the anions of two unsubstituted thenoyltrifluoroacetonate ligands, each abbreviated TTFA can be conveniently prepared by one of several methods. One method involving the ammonium salt of the β-ketoenol and the appropriate rare-earth salt is shown by J. G. Stites, et al., J. Amer. Chem. Soc. 70, 3142 (1948), incorporated by reference herein. This results in the compound Eu(III)(TTFA)$_2$(TTFA—NH$_2$).

In order to couple the above fluorescent Eu(III) complex to an antibody, the amino on the TTFA—NH$_2$ ligand must be converted to an isothiocyanate. This can be accomplished by one of several approaches which avoid low pH that could cause acid decomposition of the complex. This type of conversion has been effected by the technique of H. A. Staab and G. Walther, Ann. 657, 98, (1962), and 657, 104, (1962), incorporated by reference herein or by the alternate technique of D. Hobson et al., J. Chem. Soc. (C) 1970, 971, also incorporated by reference herein.

The actual coupling of the fluorescent Eu(III) to the antibody follows one of several variations of methods already successfully used to attach fluorescein isothiocyanates to antibodies such as the method of J. L. Riggs et al., Amer. J. Pathol., 1. 34, 1081 (1958), incorporated by reference herein, or the method of J. D. Marshall, Proc. Soc. Exp. Biol. Med. 98, 898, (1958), also incorporated by reference herein.

b. Sample Preparation. In order to utilize the unique FAB's synthesized above in a direct immunofluorescent assay of blood serum for a particular antigen, the serum is first prepared in the usual way, and the antigen is fixed on a solid substrate, exposed to and combines with the FAB specific to the antigen and excess FAB is separated away.

Various methods for isolating the antigen-FAB complex for measurement may be employed. One preferred method is the "sandwich" technique described by F. Paronetto, Proc. Soc. Exp. Biol. 113, 394, (1963), incorporated by reference herein, where a solid substrate with nonfluorescing antibody fixed on it, is exposed to the sample and substantially all the antigen in the sample combines with the antibody (which is in excess of the amount needed for the desired measurement range). The solid substrate is then immersed in a solution containing the FAB which then attaches to the antigens fixed on the substrate and the substrate is removed from excess FAB and the measurement can be made on the fluorescence from the solid substrate. This method works when the antigen has more than one binding site for antibody combination, that is, for larger molecule antigens.

For smaller molecules with only one antibody specific binding site per molecule, an indirect assay method can be used. Antigens identical to those being assayed may be bound to a solid substrate which combines chemically with the antigen in a manner which leaves the antibody specific sites exposed. Chemical procedures to accomplish this would be similar to techniques used to combine antigens to large proteins prior to injecting the conjugated antigen-protein into an animal for generating antibodies to the antigen. These procedures require a chemical binding of the antigen to a protein with the antigenic site remaining exposed to the animals immune system so that appropriate antibodies can be produced. One such example is cited in "Structural Basis of Antibody Specificity", Pressman & Goldberg, W. A. Benjamin (1968) pp. 9–10, incorporated by reference herein. A solid substrate suitable for chemically combining with an antigen, could be, for example, a polymer of styrene with side chains functionalized to match an appropriate group on the antigen to be assayed. Each antigen would then have its special solid substrate coated with identical antigen to be used in the assay for that antigen.

The solid substrate is then immersed in the solution containing the unknown amount of antigen and FAB specific to the antigen is added. The antigen in solution and antigen on the solid substrate compete for the FAB and the amount of FAB which combines with the solid substrate is inversely related to the amount of antigen in solution. The amount of FAB on the solid substrate is determined by a fluorescent measurement to be described below and the amount of antigen in solution is determined.

There are clearly many other methods for sample prepration so that the fluorescent measurement can be made.

c. Measurement of Fluorescence. In a utilization of the composition of the present invention, it is necessary to tag target antigens, the quantity of which is to be determined, with FAB which has a relatively long fluorescent decay lifetime compared with decay lifetimes of ambient substances. Once the tagging has been accomplished as described above, it is necessary to measure the fluorescence from the tagged target molecules in order to deduce the amount of target material present.

In FIG. 1, using the direct method described above, the antigen target molecules have been supported on a solid substrate and combined with the FAB of the present invention, so that the antigen-FAB complex is fixed on support 21. The tagged target substance is excited by excitation source 23 having a known output spectrum. Usually the output is in the form of a beam 25 which is substantially monochromatic, and in the present embodiment, pulsed radiation, typically from a laser is employed. The pulse duration is at least ten times shorter than the FAB fluorescence lifetime of a few hundred microseconds. We have found that a pulsed nitrogen laser operating at 3371 Å causes very strong excitation. Alternatively, the filtered and focused output from a simple pulsed gas discharge can also be used, provided its duration is much shorter than the fluorescent lifetime of the FAB.

Beam 25 is directed toward target molecules on support 21. Emission from FAB-antigen complex on substrate 21 is indicated by the dashed lines 31 which are collected by a lens 33 and passed through a filter, such as an interference filter 35 and thence to a detector 37, which is typically a photomultiplier tube. Interference filter 35 has a wavelength bandpass centered at the emission wavelength of the predominant fluorescence of the FAB and filters out excitation wavelength radiation from source 23 scattered toward detector 37.

Detector 37 which is "on" at all times produces an electrical signal proportional to the fluorescent radiation emission received and which is amplified by a linear amplifier 38 which then passes the amplified signals to a gating circuit 39, which is normally closed. The gating circuit is opened (on) and closed (off) by two signals from delay circuit 36. These two signals are generated at two fixed times after the excitation pulse is sensed by phototube 34. The resulting signal from phototype 34 starts a timing sequence in circuit 36 which then generates the delayed signals.

The amount of delay selected in the delay circuit 36 for the first signal is preferably at least 5 background fluorescent lifetimes. For example, if the lifetime of background or ambient fluorescence is 50 nanoseconds, the selected first delay is preferably at least 250 nanoseconds. If the decay of ambient fluorescence is by an exponential decay mode, 5 decay lifetimes represent a reduction in the background or ambient fluorescence to about 0.7% of its peak value.

Gating circuit 39 is kept open until the second delayed signal from delay circuit 36 arrives. This should be at a time preferably 2 decay lifetimes of the FAB, for example, approximately several hundred microseconds for rare-earth chelate FABs.

Alternatively, for cases where the background fluorescence signal is sufficiently intense to saturate the photodetector or amplifier, the photodetection system can be gated by keeping the photodetector normally "off" and gating it on and off again at the times defined by the first and second signals of the delay circuit 36.

After signal gating by the gating circuit 39, the linearly amplified signal from amplifier 38 passes into the signal processor 48 which averages the results of many pulses and which correlates the amplified signal with information characterizing the emission of known quantities of the labeled target material. The output of signal processor 48 is thereby indicative of the quantity of target molecules.

Figure 2A:
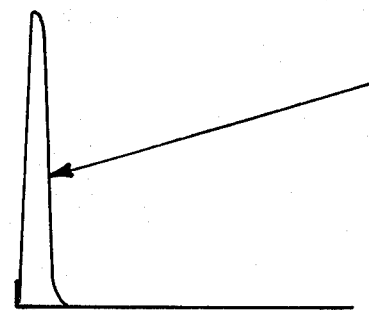
FIG. 2a is an intensity plot versus time of an excitation pulse used in operation of the apparatus of FIG. 1.
Figure 2B:
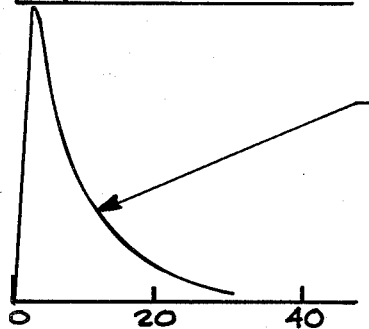
FIG. 2b is an intensity plot versus time of fluorescent emission of ambient substances which occur in operation of the apparatus of FIG. 1.
Figure 2C:
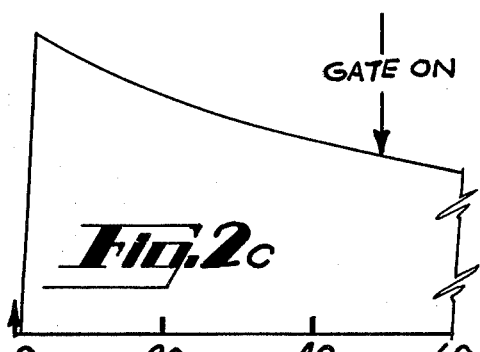
FIG. 2c is an intensity plot versus time of the emission of tagged target molecules in accord with the method of the present invention, using apparatus of the type shown in FIG. 1.
Figure 2C:
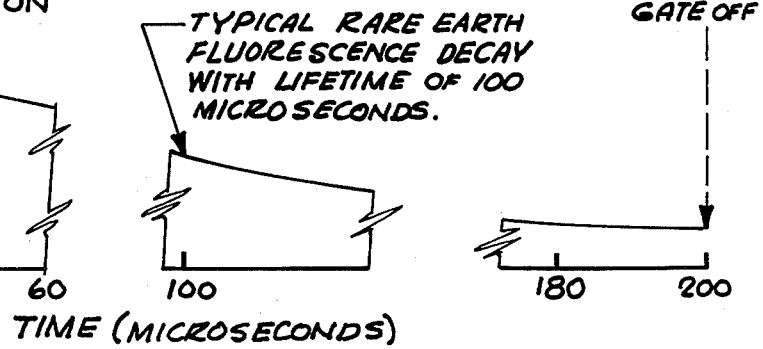

In FIG. 2c the relative intensity of rare-earth fluorescence versus time is shown. All pulses start at substantially the same time, when the excitation source is first turned on. However it should be observed that the time scale of FIG. 2c is in microseconds, whereas the time scale of FIGS. 2a and 2b is in nanoseconds. The detection system for measuring the fluorescence is kept off until the fluorescence in 2b is substantially decayed and then gated on so that only the rare-earth fluorescence can be measured and recorded. It is then gated off in preparation for the next cycle. After many cycles the fluorescence can be electronically averaged, converted to an equivalent antigen concentration and displayed.

In another application of the new FAB family, detection of spatial distribution of antigen can be enhanced by gating an image converter tube on only after background fluorescence has substantially decayed, but while FAB is still actively decaying.

While the new FAB family has been described with reference to medical diagnostic uses, other applications which require the detection of small quantities of molecules are possible.

I claim:

1. A fluorescent antibody comprising, an antibody specific to an antigen to be detected, and a fluorescent rare-earth chelate conjugated with said antibody, said rare-earth chelate consisting of a rare-earth ion coordinated by chelating ligands.

2. The fluorescent antibody of claim 1 where the rare-earth ion is Eu(III).

3. The fluorescent antibody of claim 1 where the rare-earth ion is Tb(III).

4. The fluorescent antibody of claim 2 where the chelating ligands are thenolytrifluoroacetonates and thenolytrifluoroacetonates modified for conjugation with said antibody.

5. The fluorescent antibody of claim 2 where the chelating ligands are hexafluoroacetylactonates and hexafluoroacetylacetonates modified for conjugation with said antibody.

6. The fluorescent antibody of claim 2 where the chelating ligands are benzoyltrifluoroacetonates and benzoyltrifluoroacetonates modified for conjugation with said antibody.

7. The fluorescent antibody of claim 3 where the chelating ligands are acetylacetonates and acetylacetonates modified for conjugation with said antibody.

8. A method of fluorescent detection of a target substance comprising:
tagging a target substance with a fluorescent antibody, said fluorescent antibody comprising an antibody specific to the target substance and a fluorescent rare-earth chelate conjugated with said antibody, said rare-earth chelate consisting of a rare-earth ion coordinated by chelating ligands, said rare-earth chelate having sharp spectral emission and lifetime long compared with the longest of the decay lifetimes of competing untagged ambient substances,
exciting said tagged target substance with pulses of radiation, such pulses having a duration which is short compared with the fluorescent decay lifetime of said fluorescent antibody, and
gating on a fluorescence detection system only after the fluorescence of said ambient substances has substantially decayed but while fluorescent antibody fluorescence is actively decaying.

9. The method of claim 8 where the rare-earth ion is Eu(III).

10. The method of claim 8 where the rare-earth ion is Tb(III).

11. The method of claim 9 where the chelating ligands are hexafluoroacetylacetonates and hexafluoroacetylacetonates modified for conjugation with said antibody.

12. The method of claim 9 where the chelating ligands are benzoyltrifluoroacetonates and benzoyltrifluoroacetonates modified for conjugation with said antibody.

13. The method of claim 9 where the chelating ligands are thenolytrifluoroacetonates and thenolytrifluoroacetonates modified for conjugation with said antibody.

14. The method of claim 10 where the chelating ligands are acetylacetonates and acetylacetonates modified for conjugation with said antibody.

15. A method of fluorescent detection of target substance distribution, wherein said target substance has at least one antibody combining site, the method comprising:
complexing said target substance with a fluorescent antibody, said fluorescent antibody comprising an antibody specific to the target substance and a fluorescent rare-earth chelate conjugated with said antibody, said rare-earth chelate consisting of a rare-earth ion coordinated by chelating ligands, said rare-earth chelate having sharp spectral emission and lifetime long compared with the longest of the decay lifetimes of competing untagged ambient substances, exciting said target substance-fluorescent antibody complex with pulses of radiation, each pulse having a duration which is short compared with the fluorescent decay lifetime of said fluorescent antibody, and gating on an image converter tube only after the fluorescence of said ambient substances has decayed but while fluorescent antibody fluorescence is actively decaying.

16. The method of claim 15 where the rare-earth ion is Eu(III).

17. The method of claim 15 where the rare-earth ion is Tb(III).

18. The method of claim 16 where the chelating ligands are hexafluoroacetylacetonates and hexafluoroacetylacetonates modified for conjugation with said antibody.

19. The method of claim 16 where the chelating ligands are benzoyltrifluoroacetonates and benzoyltrifluoroacetonates modified for conjugation with said antibody.

20. The method of claim 16 where the chelating ligands are thenolytrifluoroacetonates and thenolytrifluoroacetonates modified for conjugation with said antibody.

21. The method of claim 17 where the chelating ligands are acetylacetonates and acetylacetonates modified for conjugation with said antibody.

22. In fluorometry, for determining the amount of target substance present after tagging said target substance with antibody specific to the target substance, said antibody conjugated with a fluorophore, the improvement wherein said fluorophore is a fluorescent rare-earth chelate comprising a rare-earth ion coordinated by chelating ligands, said rare-earth chelate having sharp spectral emission and a fluorescent lifetime long compared with the longest of the decay lifetimes of competing untagged ambient substances.

* * * * *